(12) United States Patent
Lerner

(10) Patent No.: US 6,475,733 B1
(45) Date of Patent: Nov. 5, 2002

(54) CELL SURFACE RECEPTORS FOR THE DETECTION AND IDENTIFICATION OF COMPOUNDS

(75) Inventor: Michael R. Lerner, Dallas, TX (US)

(73) Assignee: Lerner Pharmaceuticals, Inc., Woodbridge, CT (US)

(*) Notice: Subject to any disclaimer, the term of this patent is extended or adjusted under 35 U.S.C. 154(b) by 0 days.

(21) Appl. No.: 09/647,653

(22) PCT Filed: Apr. 6, 1999

(86) PCT No.: PCT/US99/07566
§ 371 (c)(1),
(2), (4) Date: Dec. 4, 2000

(87) PCT Pub. No.: WO99/51777
PCT Pub. Date: Oct. 14, 1999

Related U.S. Application Data

(60) Provisional application No. 60/080,915, filed on Apr. 6, 1998.

(51) Int. Cl.[7] ................ C12Q 1/68; G01N 33/53; C12P 21/06
(52) U.S. Cl. ............... 435/6; 435/7.1; 435/69.1
(58) Field of Search ................ 435/6, 7.1, 69.1

(56) References Cited

U.S. PATENT DOCUMENTS

| 5,364,791 A | * | 11/1994 | Vegeto et al. | 435/320.1 |
| 5,462,856 A | * | 10/1995 | Lerner et al. | 435/7.21 |
| 5,707,798 A | * | 1/1998 | Brann | 435/6 |
| 5,874,534 A | * | 2/1999 | Vegeto et al. | 530/350 |
| 5,955,281 A | * | 9/1999 | Brann | 435/6 |

FOREIGN PATENT DOCUMENTS

| WO | 93/23431 | * | 11/1993 |
| WO | 95/02823 | * | 1/1995 |
| WO | 99/19506 | * | 4/1999 |

OTHER PUBLICATIONS

Lerner, Trends in Neuroscience 17(4), 142–146 (1994).*
McClintock et al., Brain Research Protocols 2, 59–68 (1997).*

* cited by examiner

Primary Examiner—Kenneth R. Horlick
(74) Attorney, Agent, or Firm—Wolf, Greenfield & Sacks, P.C.

(57) ABSTRACT

The invention exploits the evolutionary principles responsible for the development of the broad spectrum general odorant detector system, to create a cell-surface receptor based system capable of detecting and discriminating between thousands of chemicals. This is accomplished by subjecting a defined set of cell-surface receptors such as G-protein coupled receptors, tyrosine kinase receptors, and/or ion channels, to the types of evolutionary forces that have created the array of approximately 1,000 natural receptors used in general olfaction by higher animals. This goal is further accomplished by a 'directed evolution-in-a-test-tube' method, imposing very high rates of mutation and extremely strict selection criteria to create a sensor. The novel sensor of the present invention is selected using a sensitive melanophore-based functional bioassay.

27 Claims, No Drawings

CELL SURFACE RECEPTORS FOR THE DETECTION AND IDENTIFICATION OF COMPOUNDS

RELATED APPLICATIONS

This application is the national stage under 35 U.S.C. §371 of PCT/US99/07566 filed Apr. 6, 1999, which claims priority from Provisional U.S. patent application Serial No. 60/080,915 filed on Apr. 6, 1998, entitled DIRECTED EVOLUTION BIOSENSORS, under the International Convention. The contents of the above-identified applications are hereby expressly incorporated by reference.

FIELD OF THE INVENTION

This invention relates to biosensors that are useful in detecting chemical compounds of interest. Such biosensors are receptors such as G-protein coupled receptors, tyrosine kinase receptors, and/or ion channels, selected via mutagenesis. More specifically, the biosensors of the invention are highly specific and highly sensitive in detecting low levels of the chemical compounds of interest.

BACKGROUND OF THE INVENTION

Current methods for detecting chemical compounds of interest that offer the greatest sensitivities, such as mass spectrometry and chromatography, require cumbersome fragile equipment that need regular maintenance and calibration. These conventional assays are also limited by the specificity of the methods, the possibility of false positive detection of structurally-related compounds and the speed of chemical detection.

Natural biosensors are intricate biological systems that have evolved over billions of years to discriminate between chemical structures, to sense small numbers of molecules and to register a response in less than a second through amplification of the signal within the cell. These natural biosensors work through protein receptors.

The most common example of such highly-discriminating sensors are the olfactory receptors which are members of the G-protein coupled receptor (GPCR) superfamily (Buck, L. and Axel, R. (1991) Cell 65:175–87). The nose is the most sophisticated chemical sensor ever devised. In less than a second a nose can detect and distinguish between vast numbers of chemicals. Nature's unrelenting application of the evolutionary paradigm—selective pressure for survival of the fittest—has honed this instrument to perfection. For example, salmon use biosensors to return to their specific birth streams and a male moth, using one to three highly specific pheromone receptors can track and locate a single female several miles away. Other animals have developed the ability to distinguish thousands of distinct molecules using a complement of approximately 1,000 receptors. Dogs are routinely used for detecting explosives, illicit substances and for locating victims buried in the rubble of natural or man-made disasters.

Besides their contribution to olfaction, the importance of GPCRs to higher organisms including humans can be noted in the fact that 2,500 of the roughly 100,000 genes encoded in the human genome are for GPCRs (including the 1,000 for olfaction). An immense range of structurally diverse ligands are detected by the GPCRs. In addition to thousands of odorants comprised of naturally occurring and synthetic chemicals, GRCR ligands include structures from sugars (sucrose) to lipids (prostaglandins, leukotrienes) to peptides (from dipeptides—Nutrasweet —to proteins of 10 kD) to ions (calcium) to small aromatic molecules (melatonin, catecholamines, etc.) and even photons. This diversity of known ligands suggests that the range of chemical structures that can be detected by suitably-evolved receptors is unrestricted.

Perhaps not surprisingly, when small molecules activate GPCRs, they appear to do so by binding to amino acids located deep in their transmembrane regions. The panoply of GPCRs seen today have broadly similar structural motifs. For example, the seven membrane spanning regions of bacteriorhodopsin define an elliptical pocket (Roper, D., Jacoby, E., et al. (1994) Journal of Receptor Research 14:167–86). It is within this well that the photosensitive retinal (ligand) lies. Retinal is covalently attached to a lysine on transmembrane domain seven. This protein, along with its relatives halorhodopsin and sensory rhodopsin, comprise an ancient class of bacterial proteins that respond to photons by pumping protons and chloride ions, and by activation of a second protein respectively. All modem GPCRs apparently share the overall structure of these photoresponsive molecules including both the seven transmembrane regions and the corresponding intracellular and extracellular domains.

Small ligands, such as the retinal of rhodopsins, bind to GPCRs within wells defined by the GPCR's seven transmembrane spanning domains. This has been carefully delineated in a few cases such as the one described for the $\beta_2$ adrenergic receptor (Strader, C. D., et al., (1989) Amer. J. Resp. Cell & Molec. Biol. 1: 81–85).

Although the constitution of the seven transmembrane domains of GPCRs is limited by requirement for overall hydrophobicity, the range of amino acid variation within the transmembrane regions, from receptor to receptor, varies greatly. In all cases there is an overall pattern of hydrophobic and hydrophilic amino acids as required by the alpha helical nature of the sequences. For the most part, hydrophobic amino acids are required for the face of each transmembrane domain that faces outward towards the lipid bilayer. The amino acids facing inward show greater variability. Not surprisingly, receptors with the same ligand, such as the $\beta$1–3 receptors have greater sequence homology to each other than to disparate receptors such as those for olfaction or gastrin releasing peptide (GRP). As with an antibody selected following immunization with a particular compound, there is no clear a priori correlation between the structure of the ligand, in terms its physico-chemical properties, and the general structural features of the receptor.

The ~1,000 olfactory receptors, taken together, recognize over 10,000 different chemicals including many synthetic, non naturally occurring ones such as numerous odorous organic molecules developed by the chemical industry. Different GPCRs such as the dopamine 1 and 2 receptors share the same ligand, yet the two receptors are only somewhat related. Meanwhile, one receptor may be activated by more than one ligand with varying degrees of similarity. Both the number and diversity (or alternatively the degree of focus) of the set of chemicals used to drive the selection of the set of receptors to be used in a sensor influence the range and specificity of the final sensor.

There is a need for highly specific and highly sensitive sensors that detect, a range of chemical compounds.

There is a need for sensors that detect, within a short period of time, a range of chemical compounds.

There is an additional need for standard analytical methods to monitor products for authenticity, or compliance to standards.

SUMMARY OF THE INVENTION

The invention provides novel methods for identifying mutated receptors, novel methods for testing a sample for the presence of a ligand, novel methods for generating and identifying a fingerprint for a ligand and novel detectors for identifying the presence of a ligand which binds to a cell surface receptor. The invention also relates to methods for analyzing products based upon the presence of ligands in such products that are constituents of the products. These methods allow for providing a 'signature' for the product, enabling authentication and monitoring of products for safety, security purposes, fraud and quality control. Other aspects of the invention will be readily apparent to those of ordinary skill in the art from a reading of the detailed description of the invention.

According to one aspect of the invention, a method is provided for identifying a mutated receptor that binds the ligand. First there is obtained or there is generated a plurality of nucleic acids that code for a plurality of mutated receptors. The plurality of nucleic acids then are introduced into a plurality of cells. It is preferred that the cells in their natural state do not generate a signal when contacted with the ligand. There are different nucleic acids in different of the plurality of cells. The plurality of cells then are contacted with the ligand. An intracellular signal in a cell, generated by a ligand binding to one of the plurality of mutated receptors, is detected. The signal is indicative of the presence of a mutated receptor that binds the ligand, when the mutated receptor is selected from the group consisting of mutated G protein coupled receptors, tyrosine kinase receptors, and ion channels.

In one embodiment, the signal detected can be compared to a signal generated by a cell expressing a non-mutated receptor of the same type as the mutated receptor, thereby permitting the identification of a mutated receptor with an altered binding specificity for the ligand versus the non-mutated receptor. In another embodiment, the signal can be compared to a cell expressing a different mutated receptor which binds the ligand. In one embodiment, the ligand is not the natural ligand for the receptor.

The signals generated can be second messenger signals, which are well known to those of ordinary skill in the art. Such signals include those that result in pigment dispersion and those that cause alterations in calcium levels in the cell. Thus, the signal detected in some embodiments can be pigment dispersion and/or aggregation or calcium mediated fluorescence. Such assays are well known to those of ordinary skill in the art. Where the signal is pigment dispersion and/or aggregation, the cells preferably are melaniferous and most preferably are lower animal pigment cells. Where the signal is calcium mediated fluorescence, the cells can be virtually any cell known to those of ordinary skill in the art which have altered calcium levels as a result of the foregoing receptors. Fibroblasts, 3T3 cells, lymphocytes, keratinocytes, etc., may be used. The mutated receptors also can be cloned into yeast cells, and assays involving the propagation of the yeast known to those of ordinary skill in the art can be employed as the detectable signal. Likewise, RSAT systems such as those described in U.S. Pat. No. 5,707,798, entitled "Identification of ligands by selective amplification of cells transfected with receptors," issued Jan. 13, 1998, to Brann, M R, can also be employed.

According to another aspect of the invention, a method is provided for testing a sample for the presence of a ligand. The method involves contacting the sample with an exogenous cell surface receptor mutated to have altered binding to its natural ligand, and determining the presence of a preselected signal generated if the ligand binds to the exogenous cells surface receptor. Preferably, the mutated receptor is part of a recombinant cell expressing the receptor.

In one important embodiment, the recombinant cell is at least two recombinant cells, each expressing a respective exogenous cell surface receptor mutated differently to have differently altered binding to the natural ligand. In another important embodiment, the recombinant cell is an array of recombinant cells expressing an array of differently mutated exogenous cell surface receptors.

Important receptors, cell types, signals, and so on are as described above.

According to still another aspect of the invention, a method is provided for generating and identifying fingerprint for a ligand. The method involves generating a plurality of signals by contacting an array of recombinant cells expressing an array of exogenous mutated cell surface receptors, each of said receptors having a different selectivity or specificity for the ligand, the plurality of signals comprising the fingerprint. The fingerprint can take on any of a variety of forms. The fingerprint may be a fluorescence read-out, may be a spatial pattern, may be a graph, and so on. It is important only that the combination of the signals be derived from binding of a ligand to the array, any particular ligand generating a different pattern when contacted with the array of recombinant cells.

According to yet another aspect of the invention, a detector for identifying the presence of a ligand which binds to a cell surface receptor is provided. The detector includes a container housing a cell culture medium. Cells are contained in the container, the cells expressing a receptor which binds the ligand and producing a detectable intracellular signal when the ligand binds the receptor. The container also has an inlet port for introducing a sample containing the ligand into the container. A sensor is attached to the container for detecting the intracellular signals. In one important embodiment, the receptor is an exogenous cell surface receptor. In another important embodiment, the receptor is an exogenous cell surface receptor mutated to have altered binding to its natural ligand. In a particularly important embodiment, the cells are an array of cells expressing an array of mutated receptors.

According to a further aspect of the invention, a method is provided for determining relatedness of a sample to a standard known to be authentic or known to have at least one selected characteristic of authentic material. The method involves generating a plurality of signals for a ligand-containing standard by contacting an array of recombinant cells expressing an array of exogenous mutated cell surface receptors. Each of the receptors has a different selectivity or specificity for a ligand in the ligand-containing standard. The plurality of signals comprises a standard-fingerprint for the ligand-containing standard.

The method further involves generating a plurality of signals for a ligand-containing sample by contacting an array of recombinant cells expressing an array of exogenous mutated cell surface receptors. Each of the receptors has a different selectivity or specificity for a ligand in the ligand-containing sample. The plurality of signals comprises a sample-fingerprint for the ligand-containing sample. It is also a requirement that the array of recombinant cells expressing an array of exogenous mutated cell surface receptors contacted by the ligand-containing sample is identical to the array of recombinant cells expressing an array of exogenous mutated cell surface receptors contacted by the ligand-containing standard.

The method finally involves, comparing the sample-fingerprint with the standard-fingerprint to determine whether the ligand-containing sample is authentic.

In some embodiments, the chemical composition of the ligand-containing standard is unknown. In certain embodiments, the ligand-containing standard comprises a plurality of ligands, each ligand binding to a different array of recombinant cells expressing an array of exogenous mutated cell surface receptors. In preferred embodiments, a pattern of signals from the sample-fingerprint is compared to a pattern of signals from the standard-fingerprint, and authenticity requires the pattern of signals from the sample-fingerprint to be within a pre-selected confidence limit defining a range of a pattern of signals calculated from the pattern of signals from the standard-fingerprint. In further embodiments, the comparing step is carried out by a microprocessor. In yet further embodiments, each of the fingerprints can be a fluorescence read-out, a spatial pattern, or a graph.

According to another aspect of the invention, a computer-implemented method for determining identity of a product, is provided. The method involves receiving standard-fingerprint data produced by generating a plurality of signals for a ligand-containing standard by contacting an array of recombinant cells expressing an array of exogenous mutated cell surface receptors, each of the receptors having a different selectivity or specificity for a ligand in the ligand-containing standard. The plurality of signals comprises a standard-fingerprint for an authentic ligand-containing standard.

The method further involves, receiving sample-fingerprint data produced by generating a plurality of signals for a ligand-containing sample by contacting an array of recombinant cells expressing an array of exogenous mutated cell surface receptors, each of the receptors having a different selectivity or specificity for a ligand in the ligand-containing sample. The plurality of signals comprises a sample-fingerprint for the ligand-containing sample. It is also a requirement that the sample-fingerprint data is generated using the same array of recombinant cells expressing an array of exogenous mutated cell surface receptors contacted by the ligand-containing standard to generate the standard-fingerprint data.

The method finally involves, comparing sample-fingerprint data from the ligand-containing sample to standard-fingerprint data from the ligand-containing standard, and identity so requires the sample-fingerprint data from the ligand-containing sample to be within a pre-selected confidence limit defining a range of values calculated from the standard-fingerprint data.

In important embodiments, the computer-implemented process further comprises using a computer database for storing and making available information about standard-fingerprint data of an authentic product and includes a computer-readable medium having computer-readable logic stored thereon. The computer-readable logic comprises a plurality of records for the authentic product indicating measurements of a plurality of signals for a ligand-containing standard generated by contacting an array of recombinant cells expressing an array of exogenous mutated cell surface receptors. Each of the receptors has a different selectivity or specificity for a ligand in the ligand-containing standard. The plurality of signals comprises a standard-fingerprint for an authentic ligand-containing standard, and an indication of the product. The records are accessible using an indication of the product, wherein the step of receiving standard-fingerprint data for the authentic product includes the step of accessing the computer-readable medium using an indication of the product to retrieve the records.

According to yet another aspect of the invention, a computer database for storing and making available information about standard-fingerprint data of an authentic product, is provided. The computer database comprises a computer-readable medium having computer-readable logic stored thereon. The computer-readable logic comprises a plurality of records for the authentic product indicating measurements of a plurality of signals for a ligand-containing standard generated by contacting an array of recombinant cells expressing an array of exogenous mutated cell surface receptors, each of the receptors having a different selectivity or specificity for a ligand in the ligand-containing standard, the plurality of signals comprising a standard-fingerprint for an authentic ligand-containing standard, and an indication of the product. Means for accessing the computer-readable medium using an indication of the product to retrieve the records, are also provided.

In the foregoing discussion, the receptors, the assays and the detectors are described in connection with recombinant cells. It should be understood that this represents only a preferred embodiment, and the recombinant receptors can be otherwise provided in arrays on substrates such as microchips. The receptors may be coupled to sensing material such electrotransmissive or conductive polymers and the like. The binding of the ligand then could be detected by a secondary change in the conductive material, triggered by the binding. The ligand also simply could be labeled, and the pattern of binding detected by detecting the label. Those of ordinary skill in the art will readily recognize how arrays of receptors made according to the invention can be assembled onto substrates and used to achieve the benefits of the invention.

In any of the foregoing embodiments, the ligand can include, but is not limited to, chemical warfare agents, explosives, drugs, fragrances, impurities, environmental toxins, and/or pollutants.

These and other aspects of the invention are described in greater detail below.

DETAILED DESCRIPTION OF THE INVENTION

The invention is useful any time it is desirable to detect a ligand which binds a receptor and generates an intracellular signal. The ligand does not need to be the natural ligand for the receptor. Instead, it is a feature of the invention to create mutated receptors from molecules that are not otherwise ligands for the non-mutated receptor.

The invention is particularly useful for detecting ligands at very low concentration and which are difficult to detect. The invention by its nature lends itself to increased specificity and selectivity for such molecules. That is, receptors with desired specificities and selectivities can be created.

The invention is also useful for analyzing products based upon the presence of ligands in such products that are constituents of the products, that in turn enable authentication and monitoring of the products for fraud and quality control.

The types of molecules that can be detected include, inter alia, chemical, biological and/or radiological warfare agents, explosives, drugs, fragrances, impurities, environmental toxins and pollutants. Also included are molecules which are clinically desirable to detect, such as drug concentrations in serum or other body fluids, or levels of molecules at very low concentration in body fluids such as hormones, cytokines, neurotransmitters, proteins, lipids, carbohydrates, vitamins, minerals, pathogens and components thereof such as viral particles, etc. A comprehensive list of drugs may be found in U.S. Pat. No. 5,795,909 to Shashoua et al., issued Aug. 18, 1998, the entire disclosure of which is incorporated herein by reference. A list of pathogens may be found in PCT WO 96/22024, published Jul. 25, 1996, and claiming priority to U.S. Ser. No. 08/578,171, filed Dec. 29, 1995 to Blumberg et al., the disclosures of which are incorporated herein by reference. Chemical warfare agents are well known in the art and include, but are not limited to, cholinesterases, persistent VX (O-ethyl-S-2-diisopropylaminoethyl-methylphosphonothiolate), nonpersistent Sarin (GB)(isopropyl methyl phosphonofluoridate), Tabun (GA)(ethyl-N,N-dimethyl phosphoramidocyanidate), organosulfur agents such as mustard gas (Bis-(2-chloroethyl)sulfide or HD), pinacolyl methylphosphonofluoridate which is also known as GD, neat and thickened forms of HD and GD, organophosphate compounds which contain phosphorus double-bonded to an oxygen atom and single-bonded to a carbon atom, dichloro (2-chlorovinyl) arsine (Lewisite or agent L), bis(2(2-chloro ethylthio)ethyl) ester (agent T), hemimustard derivatives (HMOs), etc. Explosives include, but are not limited to, nitroglycerine (NG), ethylene glycol denitrate (EGDN), 2,4,6-trinitrotoluene (TNT), cyclo-1,3,5-tri-methylene-2,4,6-trinitramine (RDX or cyclonite), high melting explosives (HMX), picric acid, and the like, or explosive precursors, such as ammonium nitrate, and the like, and multi-component explosive compositions including 2-ethylhexyl nitrate and a granular solid oxidizer (See also, U.S. Pat. Nos. 5,811,726, 4,253,889, and 5,226,986). Environmental toxins and pollutants are well known in the art. Examples of such agents can be found in the Appendix D of the 1989–90 biannual report of the "Agency for toxic Substances & Disease Registry," U.S. Department of Health and Human Services, Bethesda, Md., and the publication of "Odor Thresholds for Chemicals with Established Occupational Health Standards" by TCR Environmental Consultants, East Hartford, Conn.

The invention offers speed and the capability of performing the assay outside of the lab at a test site. Devices according to the invention can be made to be hand-held.

The technology of the present invention is based in part on the prior art which shows that exogenous cell surface receptors can be coupled to intracellular signally pathways and that such signals once generated can be detected. This technology was pioneered in U.S. Pat. No. 5,462,856, to E. A. Lerner and M. R. Lerner, entitled, "Methods for Identifying Chemicals that Act As Agonists or Antagonists for Receptors and other Proteins Involved in Signal Transduction Via Pathways that Utilize G-Proteins", issued Oct. 31, 1995, the disclosure of which is incorporated herein by reference. Other aspects of the prior art and useful according to the invention are described in U.S. Pat. No. 5,601,992, entitled, "Peptide Library Format and Methods Relating Thereto", to M. R. Lerner, C. K. Jayawickreme and E. A. Lerner, issued Feb. 11, 1997, and U.S. Pat. No. 5,753,511, entitled "Automated Fingerprint Methods and Chemistry for Product Authentication and Monitoring", to Richard Selinfreund, issued May 18, 1998, the disclosures of which are incorporated herein by reference.

Particular receptors useful according to the invention are the transmembrane receptors that function through dimerization, such as tyrosine kinase receptors. Such transmembrane receptors include the receptors for the interleukins, for platelet derived growth factor, for epidermal growth factor, for fibroblast growth factor and for erythropoietin.

Another class of receptors useful according to the invention are the ion channels, in particular, the histamine gated channels, the calcium channels, the serotonin gated channels, acetylcholine (nicotinic) ion channel, potassium ion channel, and glutamate ion channels.

Another class of receptors useful according to the invention are G-protein coupled receptors. The G-protein coupled receptor families are:

Family A—receptors related to rhodopsin and the $\beta_2$-adrenergic receptor;

Family B—receptors related to the calcitonin and PTH/PTHrP receptors;

Family C—receptors related to the metabotropic glutamate receptors;

Family D—receptors related to the STE2 pheromone receptors;

Family E—receptors related to STE3 pheromone receptors; and

Family F—receptors related to the cAMP receptors.

Most of the G protein coupled receptors are named by their ligands. Ligands include the purines, nucleotides and melatonin (adenosine, cAMP, melatonin, NTPs and other related compounds) biogenic amines (and related natural ligands) such as adrenaline, dopamine, histamine, acetylcholine, noradrenaline, serotonin and other related compounds, peptides such as angiotensin, bradykinin, calcitonin, endothelin, galanin, growth hormone releasing hormone, glucagon, neurotensin, vassopresin, and other related compounds; eicosanoids; retinal-based compounds; lipids and lipid-based compounds such as cannabinoids, platelet activating factor, leukotrienes and other related compounds; excitatory amino acids and ions such as glutamate, calcium and GABA; and orphan receptors in a variety of families and groups. Another way of classifying G-protein coupled receptors is through their tissue specificity and function. One important such class is the olfactory class of G-protein coupled receptors, of which on the order of 100 already have been cloned.

According to one particular aspect of the invention, arrays of cells expressing arrays of mutated receptors are employed. An array as used herein involves at least 10, preferably at least 10 and in some embodiments 25, 100 or more different mutated receptors. An array of mutated receptors is selected whereby any particular ligand would react with the array in a manner different from any other ligand. Thus, much like olfaction, an array of receptors can be used to generate a pattern of signals which act as a fingerprint for any particular ligand.

In one aspect of the invention, a sensor is provided. The sensor in its most basic elements is a device comprising a chamber containing cells, with an inlet port for introducing a sample containing a ligand into contact with the cells. The container also can house a substrate for promoting survival and/or growth of the cells or a medium such as a food. The housing also can be provided with an exit port. Preferably, the bottom of the container upon which the cells are resting is clear, and a sensor is attached to the bottom of the container for detecting a signal generated by the cells. The sensor can be any conventional sensor for detecting electromagnetic radiation such as a CCD camera. The sensor in turn can be attached to a signal display mechanism such as an LCD or other signal display means. In this manner, when a sample containing a ligand is introduced into the chamber containing the cells, the ligand is permitted to contact the cells. If the ligand binds a receptor on the cells, then a signal is generated. The sensor detects the signal and displays the signal on the signal display. In this manner, it can be determined rapidly whether the sample contains the ligand.

The sensor can be a spectrophotometer, a fiber optic probe, a CCD camera as mentioned above, as well as any other electromagnetic sensor known to those of ordinary skill in the art. The signal display can focus the signal, amplify the signal, digitize and reproduce the signal in a readable form, and so on. Where the cells are an array of cells carrying an array of receptors, the device can be provided with a processor for processing the signal into a fingerprint of a desired display format. Modifications of the foregoing device will be apparent to those of ordinary skill in the art.

Mutated receptors are described in connection with the present invention. The methodology for mutating DNA to produce mutated receptors is well known to those of ordinary skill in the art. The receptors useful herein either already have been cloned or can be cloned. Numerous G protein coupled receptors have been cloned and are available in the prior art. Mutating the DNA encoding such receptors is now routine, using, for example, iterative PCR-based mutagenesis. Site-directed mutagenesis as described in the prior art also may be employed. Reference may be made to Sambrook et al., *Molecular Cloning: A Laboratory Manual*, Second Edition, Cold Spring Harbor Laboratory Press, 1989, for methodologies in recombinant technologies, all of which are well known to those of ordinary skill in the art. Likewise, methods of cloning such DNAs into cells is well known to those of ordinary skill in the art and described in the patents incorporated herein by reference. Further elaboration is not necessary, as these are art-recognized techniques. Likewise, the conditions for growing cells and so forth are well-known to those of ordinary skill in the art, depending on the particular cells selected.

It previously has been discovered and developed a melanophore-based biotechnology used by the pharmaceutical industry. It uses melanophores derived from frogs as a sensitive read-out system. Stimulation of receptors present on the surface of these cells results in the generation of second messenger signals leading to aggregation or dispersion of melanosome pigment granules such that the cells appear "black or white". This color change is readily detectable by one of several imaging techniques. The receptors may be endogenous to the cells or consist of plasmid cDNAs encoding exogenous receptors from any source transfected into the cells via conventional molecular biological techniques.

The present invention advances the melanophore technology and creates a detection system to recognize chemicals of interest. This goal is achieved by mutation of selected G-protein coupled receptors so as to alter their specificity. The mutant receptors will recognize specific chemicals with high specificity and sensitivity. Detection of chemical signatures of explosives, for example, can be targeted.

The present invention exploits the evolutionary principles responsible for the development of the broad spectrum general odorant detector system to create a G-protein coupled receptor (GPCR) based system capable of detecting and discriminating between thousands of chemicals. The means is to subject a defined set of G-protein coupled receptors to the types of evolutionary forces that have created the array of approximately 1,000 natural receptors used in general olfaction by higher animals. This goal is accomplished by 'directed evolution-in-a-test-tube.' The forces of evolution are mutation and selection. The speed of evolution can be increased massively in the laboratory by imposing very high rates of mutation and extremely strict selection criteria. Until recently, the goal of using nature's method to detect substances for which there are no natural biosensors seemed remote. However, a combination of events has changed the picture. First, the molecular structures of GPCR receptors have been determined (Trumpp-Kallmeyer, S., et al. (1992) J. Med. Chem. 35:3448–62; Hibert, M. F., et al. (1991) Molec. Pharm. 40:8–15; Roper, D., and Jacoby, E., et al. (1994) Journal of Receptor Research 14:167–86). Second, methods have been developed for creating very large numbers of mutant receptors (Winter, G., et al. (1994) Annual Review of Immunology 12:433–55; Waterhouse, P., et al. (1993); and Nucleic Acids Research 11:2265–6; and Hoogenboom, H. R., et al. (1992) Immunological Reviews 130:41–68). In some embodiments, mutations spanning the full length of the receptor molecule may be generated. In other important embodiments, the mutations may be generated at specific sites of the receptor molecule, for example, the inwardly facing amino acids in transmembrane regions of GPCRs, resulting in receptors with new specificities. For β-serotonin and dopamine receptors, it is believed that transmembrane regions 3–6 are preferred regions for mutations.

Development of a general purpose biosensor is accomplished by 'directed evolution-in-a-tube.' DNA that encodes ten naturally-occurring G-protein-coupled receptors which signal via the production of diacylglycerol and calcium is subjected to extensive mutation by molecular substitution to produce very large numbers of novel but related receptor genes. These receptors are expressed in melanophore cells which respond to receptor activation by producing a rapid, easily-read color change that can be detected by direct digital video imaging. An example of the pigment darkening response of melanophores to activation, includes the activation of a recombinant murine bombesin receptor, a typical GPCR that signals via calcium. Receptors can be selected by virtue of their responses to any chemicals with widely varying structures. There is no limit on the number of chemicals that could, in principal, be applied to the mutant receptor pools. The sequences of receptors that are activated by different chemicals are determined and compared to identify structural features that appear to confer increased chemical specificities. These features are selectively retained as further rounds of mutation and selection occur.

The reason for starting with ten calcium signaling GPCRs, as opposed to one, is the base of primary sequence diversity thus available from which to begin receptor mutagenesis. The receptors are those for calcium (the ligand is calcium, not to be confused with signaling via calcium), Thromboxane, Platelet Activating Factor, Acetylcholine, Glutamate (the metabotropic receptor), Epinephrine (the α-1 adrenergic receptor), Substance P, Bombesin, Substance K and Cholecystokinin. The 10 receptor start point provides receptors capable of detecting a broad range of chemical structures—ions to lipids to small organic molecules to small peptides—with a broad range of molecular weights ranging from 40 to approximately 4,000 daltons. It is expected that all of these receptors are capable of detecting molecules with molecular weights on the order of a few hundred daltons such as explosives because even the Cholecystokinin receptor, whose 33 amino acid natural ligand is the largest of any of the ligands for the receptors listed here, is capable of responding to a small benzodiezapine type molecule with a structure not related to the natural peptide ligand (Aquino, C. J., et al. (1996) Journal of Medicinal Chemistry 39(2):562–9).

Rationale for Clone Generation, Detection and Isolation

Two important factors are: 1) the ability to generate a large number of mutant receptors, and 2) the ability to select stringently for receptors that respond to chemicals of interest.

The advent of the polymerase chain reaction (PCR) makes it possible to generate an almost unlimited array of mutants. Moreover the technique can be used to mutagenise selected parts of a molecule whilst leaving other parts intact. Creating mutants is therefore not limiting. Careful design of mutagenesis strategy is however necessary since the effort required to screen for appropriately responsive receptors increases linearly with the number of mutants.

The selection process is based on an established method for expressing receptors in frog melanophores; protocols are readily available for detecting responses to ligands present at femptomole quantities in the medium bathing the cells.

The ability to identify rare clones is based on two aspects of the assay according to the present invention: low noise and repeatability. Feasibility studies (McClintock, T. S., et al. (1993) Analytical Biochemistry 209: 298–305 and other experiments some of which are described elsewhere herein), have shown that the presence of plasmid coding for a receptor present at only 1 part in 200,000 can be detected in 30,000 melanophore cells (20% of the cell covered area within a single well of a 24-well culture plate). The plasmid in the foregoing control experiments was plasmid containing a cDNA coding for the $\beta_2$-adrenergic receptor. Pigmentation of the positive cells (in the form of dispersed pigment) was observed during a 30 minute exposure to the $\beta_2$ adrenergic receptor agonist salbutamol. Following removal of the stimulant (salbutamol) and resetting of the pigment within the cells, the response of the cells to a second challenge of salbutamol was observed. The results showed the same cells that had responded (i.e., were pigmented) to the first salbutamol challenge, also responded to the second ligand challenge. Further experiments confirmed the reproducibility of the foregoing results. Besides the high reproducibility of the assay, these tests also demonstrated that the assay is highly sensitive with very low background, for example, in the foregoing control experiments, only 0–1 nonspecific responders during a given 30 minute test period were discovered. Additional evidence for the stability of the system for detecting rare clones were generated in further experiments where the cells utilized were cells which do not express the $\beta_2$-adrenergic receptor (wild type). In two successive such tests, the cells did not respond to salbutamol challenge.

Selection involves isolating receptors with the desired property, i.e. response to one or more of, for example, 192 test chemicals. In another example, we tested the sensitivity of the system by attempting the cloning of a human prostacyclin receptor from a cDNA library. The library was constructed from cDNAs transcribed from poly $A^+$ RNA extracted from a human erythroleukemia cell line that was known to express prostacyclin receptors. In this particular experiment, 26 pools of plasmids, each containing approximately 5,000 plasmid clones randomly selected from the cDNA library, were expressed in melanophores. Images containing approximately 5,000 melanophores were obtained before and after treatment with the agonist prostacyclin. Following subpooling of the positive ("black color") plasmid pool into 5 sets each containing 1,000 plasmids, the process was repeated in order to enrich signal. The subpooling of a positive pool was repeated until a pure clone coding for the receptor was isolated. Sequencing of the cDNA from the pure clone was used to confirm the clone as the human prostacyclin receptor.

Mutagenesis Strategy

Approximately $10^7$ mutants of each receptor is created by PCR mutagenesis. Changes are made selectively in those amino acids of transmembrane regions that face inwards towards the ligands. Methods for large-scale directed mutagenesis have been described and used extensively for the creation and selection of synthetic antibodies for specific ligands (Winter, G., et al. (1994) Annual Review of Immunology 12:433–55; Waterhouse, P., et al. (1993); and Nucleic Acids Research 11:2265–6; and Hoogenboom, H. R., et al. (1992) Immunological Reviews 130:41–68). In brief, oligonucleotides spanning each of the transmembrane regions and containing base changes designed to create quasi-random non-conserved amino acid substitutions are used as the basis for PCR. Because of the complexity associated with simultaneously using several degenerate oligonucleotides in terms of annealing, chain elongation and ligation, the initial PCR mutagenesis will place mutations into regions 3 and 4. Once an interim library has been constructed it will serve as the base for construction of the final library where additional mutations into regions 5 and 6 can be introduced.

Quantitative Considerations

From a practical standpoint it is possible to screen $10^6$ clones for a response to a new ligand using a single well containing transfected melanophores. In the example discussed earlier, detection of a $\beta_2$ adrenergic receptor clone against a background of 200,000 other clones, was achieved. The CCD camera employed in those experiments had a collecting area composed of 1.3 million pixels.

The number of mutant receptors to be screened against each chemical ($10^8$ with $10^7$ for each of the 10 starting receptors) is based on a number of factors and comparison with other ligand-binding biological systems such as the immune system. The production of monoclonal antibodies to any molecule be it the classic hapten dinitrophenol or a chemical such as TNT is a relatively simple task. Clearly, the repertoire of antibodies available to the murine immune system when challenged ($10^8$) is sufficient to produce an effective antibody. Antibodies can also be raised entirely in vitro using antibody phage display technology. Again, $10^6$ to $10^8$ clones need to be screened to have a high chance of generating a high-affinity antibody.

Mutant Receptor Library Construction and Screening

The mutant receptor PCR products are used to create a plasmid library in the vector J.G.3.6 developed specifically for use with the melanophore assay (Potenza, M. N. and Lerner, M. R. (1994) Nauyn-Schmiedeberg's Archives of Pharmacology 349: 11–19). Commercial high-efficiency competent cells are used to create ~$10^8$ clones from vector construct DNA.

The cDNA library is plated out onto 400 cm$^2$ plates at a density of ~250,000 per plate. Each plate represents a 'pool' and screened as sets of 4 at a time comprising 1 million clones. As a total of ~$10^7$ clones are screened for each receptor in the first round, 10 wells are required per progenitor receptor-plasmid library. Replicas of the plates are prepared and stored at −80° C. so that individual clones can be subsequently retrieved. DNA is prepared from each plate and used to transfect up to ~$4\times10^6$ melanophores. The melanophores are plated as a continuous adherent lawn within wells of 12 well microplates with approximately $4\times10^4$ cells per cm$^2$ (approximately 25% of the cells survive electroporation and the remaining melanophores are discarded). Ligands are added to the medium bathing the cells. An image of the well is captured before ligand addition and after 30 minutes of ligand exposure using a scanning stage to obtain fields of 300,000 cells from each well. Subtraction of the images will reveal the presence of cells that have undergone pigment dispersion in response to ligand. The cells are washed and re-exposed to ligand. Lawns that contain more than 10 cells that respond consistently to ligand are considered 'positive'.

Deconvoluting Positive Pools

As in the example above for isolating a clone coding for the prostacyclin receptor, each positive pool (of 1,000,000 clones) can be subdivided into its original 4 pools of 250,000 and rescreened. The process can be repeated using 10 fold smaller pools for subsequent rounds until single pure clones are obtained.

Further Mutagenesis and Selection

Once primary clones that code for receptors responding to new ligands are obtained, for example, TNT in the range of 1–10 $\mu$M, their DNA and deduced amino acid sequences can be is analyzed. Receptors that bind ligand in essentially the same orientation might be expected to share certain specific amino acid substitutions. Receptor molecules will therefore be grouped with regard to similarities in sequences. On the other hand, receptors that bind a specific ligand in a significantly different orientation are likely to show quite different but constant amino acid substitutions. This information can therefore be used to segregate receptors into different structural subclasses (perhaps reflecting the 10 original progenitor receptors). The ability to find receptors that bind ligands in different orientations by using different combinations of amino acids at different positions on different transmembrane regions is highly desirable. Biosensors which recognize the same small molecule in different orientations within the binding 'pockets' are unlikely to recognize any other single molecule with equal affinity. Therefore, ultimately, a biosensor composed of more than one variant receptor would have increased selectivity for the ligand in question and is unlikely to give false positive detection with other molecules. In other words, a combination of different receptors, several or all of which must trigger to indicate the presence of a particular ligand, could provide input for highly discriminating neural net processing and analysis of the primary sensor signal.

Allocation of receptors to subclasses can be based on common discriminating sequence features. Each distinct subclass will provide a distinct substrate for a second round of mutagenesis and selection. Those amino acids which are conserved between members of a particular subclass can be held constant while other parts of the molecule can be further modified. The second round of screening can be carried out as for the first except that the stringency of selection can be increased ten-fold to 100–1,000 nM TNT and other ligands. Once receptors meeting the new criteria are selected the process can be repeated. The goal is to develop receptors capable of recognizing TNT and other ligands in the 1–10 nM range.

Once chemical-specific receptors are generated, construction of an instrument that incorporates the biosensor commences. It is currently feasible to detect calcium increases in living cells in a few milliseconds using calcium sensitive chemicals such as Calcium Green (Eberhard M. Erne P. (1991) Biochemical & Biophysical Research Communications, 180(1):209–15; Kong, S. K., Choy, Y. M. and Lee C. Y. (1994) Biochemical & Biophysical Research Communications, 199(1):234–40). One envisioned format for the detector is a 4×4 cm array containing 1,000 wells, each with a diameter of 1 mm and containing contact inhibited fibroblasts that express one of the synthetic receptors. The pattern of calcium level elevations in response to receptor stimulation within the wells will provide chemical specific fingerprints which can be imaged with a CCD camera. The engineering of the Calcium Green signal methodology is well described and commercially available. Fluorometric screening via a CCD camera of Calcium Green based signals generated by ligand mediated GPCR based elevations in intracellular is practiced in new lead discovery programs within the pharmaceutical industry using instruments such as the FLIPR manufactured by Molecular Devices of Sunnyvale Calif.

Equivalents

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety.

I claim:

1. A method for identifying a plurality of mutated receptors that bind a ligand to produce an identifying fingerprint for the ligand, comprising:

generating a plurality of nucleic acids that encode a plurality of mutated receptors, introducing the plurality of nucleic acids into a plurality of cells, there being different nucleic acids in different of the plurality of cells, expressing the plurality of nucleic acids in the plurality of cells to produce a plurality of mutated receptors on the surface of the cells, contacting the plurality of cells with the ligand, detecting an intracellular signal in a cell generated by a ligand binding to one of the plurality of mutated receptors, the signal being indicative of the presence of a mutated receptor that binds the ligand, wherein the mutated receptor is selected from the group consisting of mutated G-protein coupled receptors, tyrosine kinase receptors and ion channels, and selecting a plurality of mutated receptors based upon the generated intracellular signals to produce an identifying fingerprint for the ligand.

2. The method of claim 1, wherein the signal detected is compared to a signal generated by a cell expressing a non-mutated receptor of the same type as the mutated receptor, thereby permitting the identification of a mutated receptor with an altered binding specificity for the ligand versus the non-mutated receptor.

3. The method of claim 1, wherein the signal is compared to a cell expressing a different mutated receptor which binds the ligand.

4. The method of claim 1, wherein the ligand is not the natural ligand for the receptor.

5. The method of claim 1, wherein the ligand is selected from the group consisting of chemical warfare agents, explosives, drugs, fragrances, impurities, environmental toxins and pollutants.

6. The method according to any of claims 1–5, wherein the signals generated are second messenger signals.

7. The method of claim 6, wherein the second messenger signals result in pigment dispersion or aggregation.

8. The method of claim 7, wherein the cells are melaniferous.

9. The method of claim 8, wherein the cells are lower animal pigment cells.

10. The method of claim 6, wherein the second messenger signals cause alterations in calcium levels in the cell and the signal is calcium mediated fluorescence.

11. A method for testing a sample for the presence of a ligand comprising:

contacting the sample with a plurality of recombinant cells expressing a plurality of exogenous cell surface receptors, each receptor mutated to have altered binding to its natural ligand, and determining the presence of a preselected signal generated if the ligand binds to the plurality of exogenous cell surface receptors.

12. The method of claim 11, wherein the recombinant cell is at least two recombinant cells, each expressing a respective exogenous cell surface receptor mutated differently to have differently altered binding to the natural ligand.

13. The method of claim 11, wherein the recombinant cell is an array of recombinant cells expressing an array of differently mutated exogenous cell surface receptors.

14. The method of claim 11, wherein the mutated exogenous cell surface receptor is selected from the group consisting of mutated G-protein coupled receptors, tyrosine kinase receptors and ion channels.

15. The method of claim 11, wherein the signal is compared to a cell expressing a different mutated receptor which binds the ligand.

16. The method of claim 11, wherein the ligand is not the natural ligand for the receptor.

17. The method of claim 11, wherein the ligand is selected from the group consisting of chemical warfare agents, explosives, drugs, fragrances, impurities, environmental toxins and pollutants.

18. The method according to any of claims 11–17, wherein the signals generated are second messenger signals.

19. The method of claim 18, wherein the second messenger signals result in pigment dispersion or aggregation.

20. The method of claim 19, wherein the cells are melaniferous.

21. The method of claim 20, wherein the cells are lower animal pigment cells.

22. The method of claim 11, wherein the second messenger signals cause alterations in calcium levels in the cell and the signal is calcium mediated fluorescence.

23. A method for generating an identifying fingerprint for a ligand comprising:
  contacting an army of recombinant cells expressing an array of exogenous mutated cell surface receptors with a ligand to generate a plurality of signals, each of said receptors having a different selectivity or specificity for the ligand, and
  selecting a plurality of the generated signals to produce an identifying fingerprint for the ligand.

24. The method of claim 23, wherein the fingerprint is a fluorescence read-out, a spatial pattern, or a graph.

25. The method of claim 23, wherein the ligand is selected from the group consisting of chemical warfare agents, explosives, drugs, fragrances, impurities, environmental toxins and pollutants.

26. A method for determining relatedness of a sample to a standard known to be authentic or known to have at least one selected characteristic of authentic material, the method comprising:
  generating a plurality of signals for a ligand-containing standard by contacting an array of recombinant cells expressing an array of exogenous mutated cell surface receptors with a ligand-containing standard, each of said receptors having a different selectivity or specificity for a ligand in the ligand-containing standard, the plurality of signals comprising a standard-fingerprint for the ligand-containing standard,
  generating a plurality of signals for a ligand-containing sample by contacting an array of recombinant cells expressing an array of exogenous mutated cell surface receptors with a ligand-containing sample, each of said receptors having a different selectivity or specificity for a ligand in the ligand-containing sample, the plurality of signals comprising a sample-fingerprint for the ligand-containing sample, wherein the array of recombinant cells expressing an array of exogenous mutated cell surface receptors contacted by the ligand-containing sample is identical to the array of recombinant cells expressing an array of exogenous mutated cell surface receptors contacted by the ligand-containing standard, and
  comparing the sample-fingerprint with the standard-fingerprint to determine whether the ligand-containing sample is authentic.

27. A computer-implemented method for determining the identity of a product, comprising:
  receiving standard-fingerprint data produced by generating a plurality of signals for a ligand-containing standard by contacting an array of recombinant cells expressing an array of exogenous mutated cell surface receptors with a ligand-containing standard, each of said receptors having a different selectivity or specificity for a ligand in the ligand-containing standard, the plurality of signals comprising a standard-fingerprint for the ligand-containing standard:
  receiving sample-fingerprint data produced by generating a plurality of signals for a ligand-containing sample by contacting an array of recombinant cells expressing an array of exogenous mutated cell surface receptors with a ligand-containing sample, each of said receptors having a different selectivity or specificity for a ligand in the ligand-containing sample, the plurality of signals comprising a sample-fingerprint for the ligand-containing sample, wherein the sample-fingerprint data is generated using the same array of recombinant cells expressing an array of exogenous mutated cell surface receptors contacted by the ligand-containing standard to generate the standard-fingerprint data; comparing sample-fingerprint data from the ligand-containing sample to standard-fingerprint data from the ligand-containing standard, and wherein identity requires the sample-fingerprint data from the ligand-containing sample to be within a pre-selected confidence limit defining a range of values calculated from the standard-fingerprint data.

* * * * *

UNITED STATES PATENT AND TRADEMARK OFFICE
CERTIFICATE OF CORRECTION

PATENT NO. : 6,475,733 B1
DATED : November 5, 2002
INVENTOR(S) : Michael R. Lerner It is certified that error appears in the above-identified patent and that said Letters Patent is hereby corrected as shown below:

Column 15,
Line 37, delete "army" and insert -- array --.

Signed and Sealed this

First Day of April, 2003

JAMES E. ROGAN
*Director of the United States Patent and Trademark Office*